(12) United States Patent
Tunc

(10) Patent No.: US 6,231,810 B1
(45) Date of Patent: May 15, 2001

(54) SPECIAL CYCLE FOR ETHYLENE OXIDE STERILIZATION

(75) Inventor: Deger C. Tunc, East Brunswick, NJ (US)

(73) Assignee: Stryker Technologies Corporation, Kalamazoo, MI (US)

( * ) Notice: Subject to any disclaimer, the term of this patent is extended or adjusted under 35 U.S.C. 154(b) by 0 days.

(21) Appl. No.: 09/296,068

(22) Filed: Apr. 21, 1999

(51) Int. Cl.$^7$ .................................................. A61L 2/20
(52) U.S. Cl. ................................. 422/34; 422/30
(58) Field of Search .................. 422/2, 27, 33, 422/34, 30

(56) References Cited

U.S. PATENT DOCUMENTS

| | | | |
|---|---|---|---|
| 4,203,943 | 5/1980 | Gillis et al. | 422/27 |
| 4,410,492 | * 10/1983 | Kaye | 422/34 |
| 4,671,936 | 6/1987 | Barron | 422/55 |
| 4,770,851 | * 9/1988 | Joslyn | 422/34 |
| 4,812,292 | * 3/1989 | Joslyn | 422/2 |
| 4,822,563 | * 4/1989 | Joslyn | 422/33 |
| 4,971,761 | 11/1990 | Johnson | 422/34 |
| 5,464,580 | * 11/1995 | Popescu et al. | 422/34 |
| 5,554,437 | 9/1996 | Gupta et al. | 442/361 |
| 5,800,542 | 9/1998 | Li | 424/423 |
| 5,830,409 | * 11/1998 | Childers et al. | 422/30 |

* cited by examiner

*Primary Examiner*—David A. Redding
*Assistant Examiner*—Theresa T. Snider
(74) *Attorney, Agent, or Firm*—Lerner, David, Littenberg, Krumholz & Mentlik, LLP

(57) ABSTRACT

A method for reducing residual ethylene oxide levels in sterilized goods by reacting the residual ethylene oxide with water after the sterilization reaction is completed, thus converting some of the ethylene oxide into ethylene glycol according to the formula (I):

FORMULA (I)

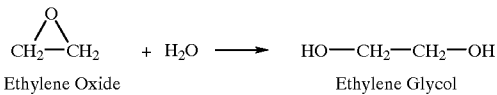

The sterilizable material may be subjected to deep vacuum degassing following the reaction of formula (I).

25 Claims, 4 Drawing Sheets

EFFECT OF DEEP VACUUM DEGASSING OF PLATES AT 10-7 TORR, 37°C ON ETHYLENE OXIDE RESIDUE AT 1 WEEK

EFFECT OF DEEP VACUUM DEGASSING OF PLATES AT $10^{-7}$ TORR, 37°C ON ETHYLENE OXIDE RESIDUE AT 1 WEEK

EFFECT OF DEEP VACUUM DEGASSING OF PLATES AT $10^{-7}$ TORR, 37°C ON ETHYLENE OXIDE RESIDUE AT 2 WEEKS

SPECIAL CYCLE FOR ETHYLENE OXIDE STERILIZATION

FIELD OF THE INVENTION

This invention relates to procedures for chemical gas sterilization and for reducing the residue remaining on the product following standard chemical gas sterilization. In particular embodiments, the invention is directed to ethylene oxide sterilization, and provides an improved method to reduce ethylene oxide residue in a product which has been sterilized by ethylene oxide gas.

BACKGROUND OF THE INVENTION

Many fields of applied biological sciences, notably the health care professions, utilize biocidal gasses to effect chemical sterilization. Chemical sterilization with a biocidal agent such as ethylene oxide is often utilized to sterilize heat sensitive goods that could not tolerate high temperature sterilization. For example, biocidal gas sterilization is routinely used for health care products such as bioabsorbable devices, catheters, introducers, stents and laparoscopes.

One type of biocidal gas sterilization is ethylene oxide sterilization, which is a well established method used by both hospitals and manufacturers of sterile goods. This process utilizes ethylene oxide gas adjusted to a certain humidity, temperature, and concentration in an inert gas in an enclosed chamber to kill microbial spores, vegetative bacteria and other microorganisms.

The penetration of the ethylene oxide, as well as the humidification and heating of the goods to be sterilized, is carried out more effectively if air is first evacuated from both the sterilization chamber and the packaged or wrapped goods. This evacuation of air and the addition of moisture is known as "conditioning" of the goods to be sterilized and is generally done prior to introduction of the ethylene oxide, which is subsequently introduced to the chamber to a predetermined pressure, usually above atmospheric pressure. These procedures are more fully described in U.S. Pat. Nos. 4,971,761; 4,203,942; and 4,671,936, all of which are incorporated by reference.

Another method of sterilization is gamma irradiation sterilization. See, for example, U.S. Pat. Nos. 5,800,542 and 5,554,437, all of which are incorporated by reference. The gamma irradiation of biologic materials under sterilization conditions is generally 25 kGy. However, most polymeric materials including biopolymers are sensitive to gamma irradiation. The polymer chains are degraded by chain scission due to the high energy gamma rays. Under most sterilization dose conditions, the net result of gamma irradiation is a reduction of molecular weight of the polymer. This gamma irradiation induced degradation can last for a long period of time by the entrapped free radicals produced within the polymeric material.

The main advantage of ethylene oxide sterilization over gamma irradiation sterilization, particularly in sterilizing sensitive materials such as bioabsorbable devices, is that ethylene oxide sterilization does not degrade the bioabsorbable polymer to any significant extent, whereas gamma irradiation sterilization does degrade it.

Ethylene oxide, while an efficient low temperature sterilant, is an irritant that must be purged to the maximum extent possible from the packs containing the articles to be sterilized, and from the articles themselves. Residue in the product which has been sterilized by ethylene oxide gas is a concern from a biocompatability and safety point of view, therefore, the amount of this residue has to be minimized.

The FDA requirements for small bioabsorbable polymer devices, i.e. less than 10 grams, is below 250 parts per million ("ppm") ethylene oxide. The normal ethylene oxide sterilization cycle leaves ethylene oxide residue levels of 1000–2400 ppm depending on the sterilization conditions. Removal of this residual ethylene oxide is routinely accomplished by an aeration procedure where the sterilized goods are aerated in a chamber for a period of time sufficient to remove substantially all traces of the sterilant gas.

It is well known in the art that both the initial ethylene oxide amount introduced into a sterilizer and its dwell time in the sterilizer affect the amount of residual ethylene oxide in the device, particularly for devices comprised of amorphous polymers.

What is needed is an improved method by which the amount of residual ethylene oxide can be reduced to acceptable levels, while not degrading sensitive materials, such as bioabsorbable devices.

SUMMARY OF THE INVENTION

The present invention comprises a method for a biocidal gas sterilization process wherein a product is sterilized with a biocidal gas, such as ethylene oxide gas, and a portion of the biocidal gas remaining after the sterilization process is completed (the residual biocidal gas) is reacted with water, thus converting a portion of the residual biocidal gas to a glycol.

For example, where the biocidal gas is ethylene oxide, the process of the present invention may be employed to reduce the residual ethylene oxide while simultaneously keeping the amount of ethylene glycol below the acceptable level of 5000 ppm required by the FDA. Deep vacuum degassing after sterilization and the reaction of a portion of the residual ethylene oxide with water reduces the residual ethylene oxide even further.

In the preferred embodiment, the present invention provides a novel method for reducing the residual ethylene oxide level following ethylene oxide sterilization of sterilizable material by reacting in the sterilization chamber the residual ethylene oxide with water after the sterilization process is completed, thus converting a portion of the ethylene oxide into ethylene glycol according to the formula (I):

FORMULA (I)

Ethylene Oxide        Ethylene Glycol

In one embodiment, the water to be reacted with the residual ethylene oxide is introduced into the sterilization chamber in the form of steam. The maximum overall temperature of a sterilizable good reached during the injection of steam is about 49° C.

In another embodiment, the sterilizable material is subjected to deep vacuum degassing following the reaction of formula (I).

The present invention may be utilized to sterilize many types of products. In certain embodiments, the sterilized products include materials that can not withstand temperatures above about 49° C.

DETAILED DESCRIPTION OF THE INVENTION

Figure 1:
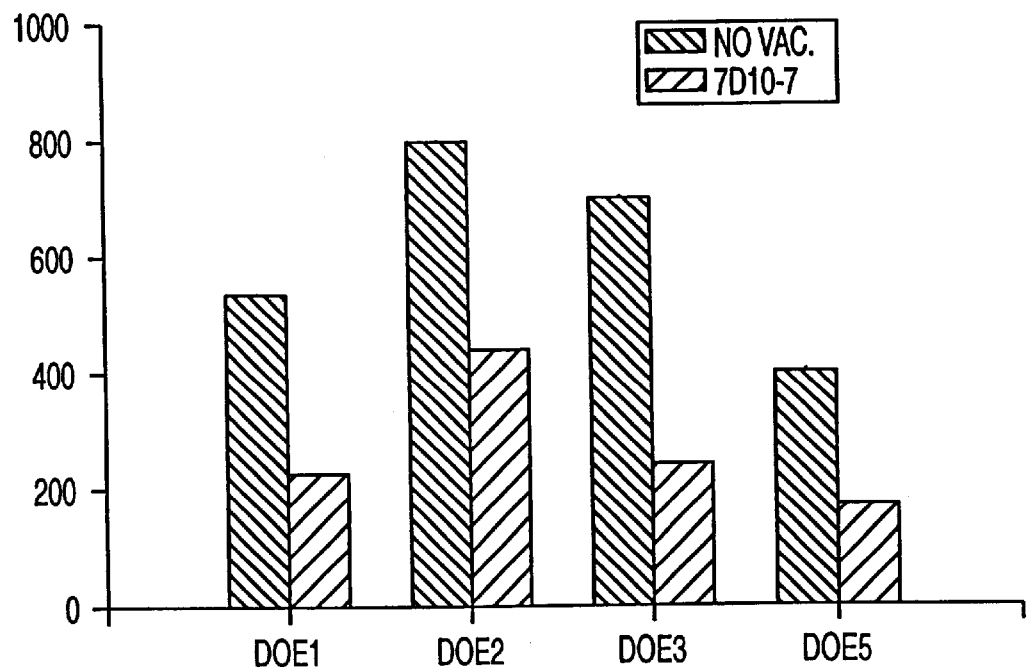
FIG. 1 illustrates the effect of deep vacuum degassing of plates at $10^{-7}$ Torr, 37° C. on ethylene oxide residue after 7 days.

The present invention relates to a new method for reducing the residual biocidal gas levels following biocidal gas sterilization of a sterilizable good or material by reacting the residual biocidal gas with water after the sterilization reaction is completed. In its preferred embodiment, the present invention comprises reacting residual ethylene oxide gas with water.

In its preferred embodiment, the present invention comprises a method for an ethylene oxide sterilization process wherein a product is sterilized with ethylene oxide gas, and the ethylene oxide remaining after the sterilization reaction is completed (the residual ethylene oxide) is reacted with water, thus converting a portion of the ethylene oxide to ethylene glycol, thereby reducing the residual ethylene oxide while simultaneously keeping the amount of ethylene glycol below the acceptable level of 5000 ppm required by the FDA.

The reaction of a portion of the residual ethylene oxide with water to form ethylene glycol proceeds according to the formula (I):

FORMULA (I)

In the present invention, the initial ethylene oxide concentration within the sterilization chamber can be in a range of about 300 mg/l to about 800 mg/l, preferably a range of about 400 mg/l to about 700 mg/l and most preferably about 600 mg/l.

In the present invention, the dwell time, i.e. the period of time during which the sterilizable good undergoes sterilization in the presence of ethylene oxide gas, can be in a range of about 3 seconds to about 10 hours, preferably a range of about 0.5 hour to about hours and most preferably about 2½ hours.

In the present invention, the duration of the reaction of residual ethylene oxide with water following the sterilization process can be in a range of about 30 minutes to about 15 or more hours, preferably a range of about 3 hours to about 13 hours and most preferably about 10 hours.

The present invention also preferably comprises the step of deep vacuum degassing of the sterilization chamber following the reaction of residual ethylene oxide and water. In the present invention, the time of deep vacuum degassing can be in a range of about 1 day to about 3 weeks, and preferably about 2 to about 3 weeks.

In the present invention, the pressure of the deep vacuum degassing can be in a range of about $10^{-6}$ Torr to about $10^{-8}$ Torr, and preferably about $10^{-7}$ Torr.

In the present invention, the temperature within the vacuum chamber during deep vacuum degassing can be in a range of about 20° C. to about 55° C., preferably a range of about 20° C. to about 49° C. and most preferably about 37° C.

Sterilizable goods include devices manufactured from polymeric material such as, but not limited to, an amorphous polymer, a semicrystalline polymer, and in particular polymers, both bioabsorbable and non-bioabsorbable polymers, such as those used in the applied biological sciences. By way of example, but not limitation, such devices would include bioabsorbable medical devices, such as plates, screws, pins, suture anchors, tacks, meniscus arrows, mesh, rods, spinal cages, bone plugs, facial plates, sutures, catheters, stents, sheaths and any health care product made of a polymeric material which may be used in health care facilities such as hospitals, medical offices, dental offices, podiatry offices, veterinary offices, medical laboratories, dental laboratories and the like.

Examples of bioabsorbable polymers include homo or copolymer or terpolymers of L-lactides, D-lactides, glycolides, capro-lactones, polydioxanones, tyrosine derivatives, polyorthoesthers, polyphosphazenes and other amorphous polymers.

In accordance with one embodiment of the invention, a sterilizable good is packaged in an inner pouch which is then packaged in an outer pouch in a manner well known in the industry. This packaged sterilizable good is sterilized in a sterilization chamber at an ethylene oxide concentration in a range of about 300 mg/l to about 800 mg/l, preferably a range of about 400 mg/l to about 700 mg/l and most preferably about 600 mg/l for a dwell time in a range of about 3 seconds to about 10 hours, preferably a range of about 0.5 hour to about 5 hours and most preferably about 2½ hours and then subjected to post sterilization treatment with moisture according to Formula (I) for an amount of time in the range of about 30 minutes to about 15 or more hours, preferably a range of about 3 hours to about 13 hours and most preferably about 10 hours, thus reducing the amount of residual ethylene oxide.

In another embodiment, a sterilizable good is packaged in an inner pouch which is then packaged in an outer pouch in a manner well known in the industry. This packaged sterilizable good is sterilized in a sterilization chamber at an ethylene oxide concentration in a range of about 300 mg/l to about 800 mg/l, preferably a range of about 400 mg/l to about 700 mg/l and most preferably about 600 mg/l for a dwell time in a range of about 3 seconds to about 10 hours, preferably a range of about 0.5 hour to about 5 hours and most preferably about 2½ hours and then subjected to post sterilization treatment with about 10 hours of pulsed or continuous steam at a pressure of about 1.0 to about 1.6 psia, preferably a pressure of about 1.3 to about 1.4 psia and a temperature of about 110 to about 125° F., preferably about 118 to about 120° F. At this pressure and temperature, the steam condenses to moisture before the overall temperature of the sterilizable good rises above 49° C.

In another embodiment, a sterilizable good is packaged in an inner pouch which is then packaged in an outer pouch in a manner well known in the industry. This packaged sterilizable good is sterilized in a sterilization chamber at an ethylene oxide concentration of about 600 mg/l ethylene oxide concentration and about 2½ hours dwell time, and then subjected to a post sterilization treatment with about 10 hours of pulsed or continuous steam at a pressure and temperature wherein the steam condenses to moisture before the overall temperature of the sterilizable good rises above 49° C., followed by deep vacuum degassing of about $10^{-7}$ Torrs and about 37° C. for about one week to about two weeks.

In another embodiment, a sterilizable good is packaged in an inner pouch which is then packaged in an outer pouch in a manner well known in the industry. This packaged sterilizable good is sterilized in a sterilization chamber at an ethylene oxide concentration of about 600 mg/l ethylene oxide concentration and about 2½ hours dwell time and then subjected to a post sterilization treatment with about 10 hours of pulsed or continuous steam at a pressure and temperature wherein the steam condenses to moisture before the overall temperature of the sterilizable good rises above 49° C., followed by deep vacuum degassing of about $10^{-7}$ Torrs and about 37° C. for about 2 to 3 weeks.

In another embodiment, a sterilizable material is placed in a sterilization chamber at an ethylene oxide concentration of about 600 mg/l, for about 2½ hours dwell time; and then subjecting the sterilizable material to a post sterilization treatment with about 10 hours of pulsed or continuous steam at about 1.3 to about 1.4 psia pressure and about 118° F. to about 120° F. followed by deep vacuum degassing of about $10^{-7}$ Torr and about 37° C. for about 2 to 3 weeks.

The method is characterized by the following example, which is meant to illustrate, but not to limit the present invention.

EXAMPLE 1

A straight, 6 hole, 2 mm craniofacial plate bioabsorbable device was fabricated by injection molding using a terpolymer, poly-(L-lactide/D-lactide/glycolide) having 85/5/10 molar ratio of the three monomers in a manner well known in the industry. The plate was not annealed. The plate was measured dimensionally, and weighed before being packaged in an inner pouch which itself was packaged in a foil pouch in a manner well known in the industry. The package was then sterilized utilizing ethylene oxide in a manner well known to those in the industry.

Sixteen design of experiment (DOE) runs were conducted utilizing multiple packages all prepared in the same manner. Three independent variables: ethylene oxide concentration, ethylene oxide dwell time and the time period for reacting residual ethylene oxide with steam ("steam time") were varied, as summarized in Table 1. The steam was introduced at a pressure wherein the steam condensed to moisture before the overall temperature of the sterilizable good rose above 49° C.

TABLE 1

| | STERILIZATION CONDITIONS | | |
|---|---|---|---|
| DOE # | E.O. Concentration mg/l | E.O. Dwell Time Hours | Steam Exposure Hours |
| 1 | 500 | 5 | 15.00 |
| 2 | 600 | 7.5 | 12.00 |
| 3 | 500 | 5 | 0.00 |
| 4 | 600 | 7.5 | 12.00 |
| 5 | 600 | 2.5 | 12.00 |
| 6 | 400 | 7.5 | 12.00 |
| 7 | 669 | 5 | 7.50 |
| 8 | 500 | 5 | 7.50 |
| 9 | 500 | 5 | 7.50 |
| 10 | 400 | 2.5 | 3.00 |
| 11 | 600 | 2.5 | 3.00 |
| 12 | 500 | 9.2 | 7.50 |
| 13 | 400 | 2.5 | 12.00 |
| 14 | 675.9 | 7.5 | 3.00 |
| 15 | 332 | 5 | 7.50 |
| 16 | 500 | 0.000833 | 7.50 |

The residual ethylene oxide level on the device was measured after the sterilization process and both prior to and after deep vacuum degassing. The mechanical properties of the device, chemical degradation of the device, and the gross effect on the device were measured after deep vacuum degassing.

In Runs # 2, 12, and 14 the total sample devices were additionally tested for ethylene chlorohydrin and for ethylene glycol. The ethylene chlorohydrin and ethylene glycol were extracted using solvents and the amounts determined using procedures well known to those skilled in the art.

To determine the residual ethylene oxide, an exhaustive extraction was performed, followed by head space analysis by gas chromatography outlined by the Association for the Advancement of Medical Instrumentation (AAMI), procedures well known to those in the industry.

To determine whether there was any degradation of the polymer comprising the device, inherent viscosity determination of the devices before and after ethylene oxide sterilization and steam treatment was done utilizing capillary glass viscometers and methods well known to those in the industry.

Mechanical testing of the plates before and after sterilization was done by a static three point bending test, the details of which are well known to those in the industry.

In order to determine if the application of deep vacuum would reduce the residual ethylene oxide level in the product further, samples from all of the DOE Runs were evacuated in a specially built deep vacuum chamber. The vacuum level was $10^{-7}$ Torrs and the chamber jacket temperature was 37° C. Samples were taken out of the chamber after one and two weeks of evacuation.

Ethylene oxide residues of three samples from each DOE run after sterilization utilizing the present invention are shown in Table 2, along with ethylene chlorohydrin and ethylene glycol content of some of the samples.

TABLE 2

Ethylene Oxide (EO), Ethylene Chlorohydrin (DC) & Ethylene Glycol (EG) Content after Sterilization

| DOE # | E.O. Residue PPM | | | Mean | Std. Dev. | E.C. Residue, PPM | | | E.G. Residue, PPM | | |
|---|---|---|---|---|---|---|---|---|---|---|---|
| 1 | 420 | 690 | 490 | 533.3 | 140.1 | | | | | | |
| 2 | 850 | 730 | 820 | 800.0 | 62.4 | | | | | | |
| 3 | 650 | 720 | 720 | 696.7 | 40.4 | <7 | <7 | <7 | <36 | <36 | <36 |
| 4 | 1600 | 1200 | 1600 | 1466.7 | 230.9 | | | | | | |
| 5 | 450 | 460 | 303 | 404.3 | 87.9 | | | | | | |
| 6 | 540 | 580 | 520 | 546.7 | 30.6 | | | | | | |
| 7 | 680 | 690 | 650 | 673.3 | 20.8 | | | | | | |
| 8 | 490 | 500 | 505 | 498.3 | 7.6 | | | | | | |
| 9 | 540 | 530 | 530 | 533.3 | 5.8 | | | | | | |
| 10 | 240 | 190 | 170 | 200.0 | 36.1 | | | | | | |
| 11 | 402 | 460 | 350 | 404.0 | 55.0 | | | | | | |
| 12 | 1140 | 980 | 1000 | 1040.0 | 87.2 | <10 | <10 | <9 | <48 | <47 | <49 |
| 13 | 250 | 240 | 230 | 240.0 | 10.0 | | | | | | |
| 14 | 1530 | 1260 | 1590 | 1460.0 | 175.8 | <10 | <10 | <10 | 46 | 110 | 110 |
| 15 | 304 | 320 | 310 | 311.3 | 8.1 | | | | | | |
| 16 | 54 | 63 | 56 | 57.7 | 4.7 | | | | | | |

The data from Tables 1 and 2 is compiled below in Table 3.

TABLE 3

Ethylene Oxide (EO) Residue, Steam Time and Ethyl Oxide Concentration Times Steam Time

| | EO RESIDUE, PPM. | STEAM TIME, HRS. | CONCENTRATION X STEAM TIME, MG/L. X HRS. |
|---|---|---|---|
| 1 | 533.3 | 15. | 2500 |
| 2 | 800.0 | 12 | 4500 |
| 3 | 696.7 | 0 | 2500 |
| 4 | 1466.7 | 3 | 4500 |
| 5 | 404.3 | 12 | 1500 |
| 6 | 546.7 | 12 | 3000 |
| 7 | 673.3 | 7.5 | 3345 |
| 8 | 498.3 | 7.5 | 2500 |
| 9 | 533.3 | 7.5 | 2500 |
| 10 | 200.0 | 3 | 1000 |
| 11 | 404.0 | 3 | 1500 |
| 12 | 1040.0 | 7.5 | 4600 |
| 13 | 240.0 | 12 | 1000 |
| 14 | 1460.0 | 3 | 5069.25 |
| 15 | 311.3 | 7.5 | 1660 |
| 16 | 57.7 | 7.5 | .4165 |

Figure 4:
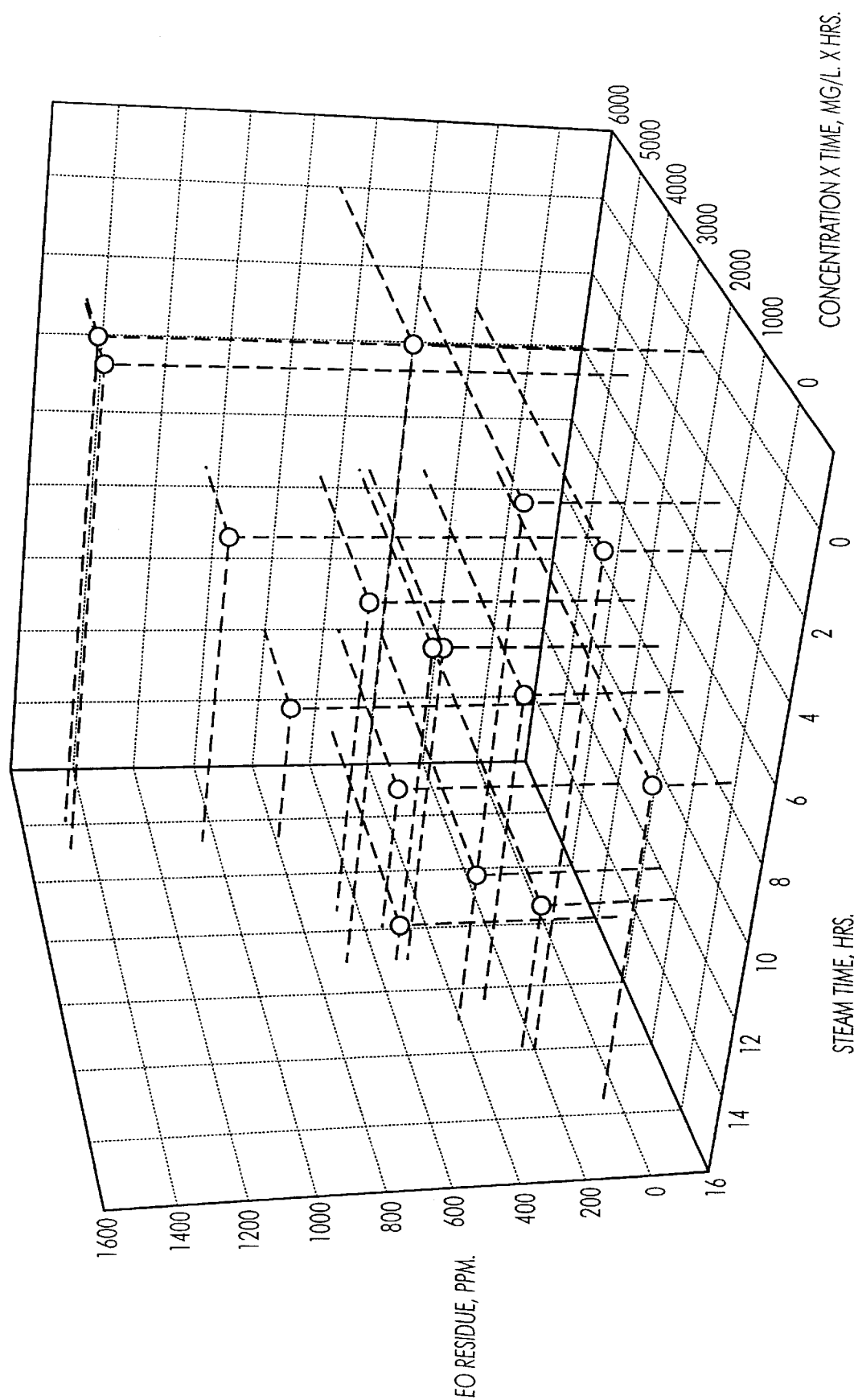
FIG. 4 is a three dimensional graph of residual ethylene oxide (x-axis) versus steam time (y-axis) versus (ethylene oxide concentration multiplied by sterilization dwell time) (z-axis).

The above data from Table 3 was plotted on a three dimensional graph which is illustrated in FIG. 4. FIG. 4 sets forth a plot of residual ethylene oxide (x-axis) versus steam time (y-axis) versus (ethylene oxide concentration multiplied by sterilization dwell time)(z-axis).

The data shows that the residual ethylene oxide level is dependent upon the ethylene oxide concentration and ethylene oxide dwell time in the sterilizer, results already well known in the prior art. The data also shows that the steam time of the present invention influences the residual ethylene oxide level, especially in the higher resultant values of the multiplication of the ethylene oxide concentration and dwell times.

Results of the inherent viscosity tests of ten samples from each DOE run is shown in Table 4. The inherent viscosity of the plates before the sterilization was 1.64±0.47 dl/g.

TABLE 4

Inherent Viscosities

| | | I.V., dl/g |
|---|---|---|
| DOE # | MEAN | STD. DEV. |
| 1 | 1.79 | 0.05 |
| 2 | 1.75 | 0.13 |
| 3 | 1.53 | 0.46 |
| 4 | 1.66 | 0.09 |
| 5 | 1.75 | 0.11 |
| 6 | 1.74 | 0.1 |
| 7 | 1.69 | 0.08 |
| 8 | 1.74 | 0.11 |
| 9 | 1.71 | 0.09 |
| 10 | 1.23 | 0.15 |
| 11 | 1.72 | 0.08 |
| 12 | 1.75 | 0.28 |
| 13 | 1.61 | 0.27 |
| 14 | 1.67 | 0.36 |
| 15 | 1.81 | 0.36 |
| 16 | 1.81 | 0.34 |

It can be concluded that neither the ethylene oxide concentration; the dwell time; nor the steam time had any statistically significant affect on the inherent viscosity of the bioabsorbable plate material.

Results from the mechanical testing of the plates are summarized in Table 5.

TABLE 5

Strength and Stiffness for Three Point Bend Testing of Plates

| DOE Run # | Number of Samples Tested | Specimen Length (mm) | Strength (Peak Load) (N) | Stiffness (Slope) (N/mm) |
|---|---|---|---|---|
| 1 | 10 | (not recorded) | 27.1 ± 1.3 | 19.5 ± 1.3 |
| 2 | 10 | (not recorded) | 27.7 ± 2.0 | 19.4 ± 1.3 |
| 3 | 10 | (not recorded) | 28.1 ± 1.9 | 18.5 ± 0.9 |
| 4 | 10 | (not recorded) | 28.1 ± 1.7 | 19.5 ± 1.0 |
| 5 | 10 | (not recorded) | 28.5 ± 1.4 | 19.6 ± 0.8 |
| 6 | 10 | 36.38 ± 0.18 | 28.0 ± 1.8 | 19.9 ± 1.3 |
| 7 | 10 | 36.46 ± 0.18 | 28.2 ± 1.3 | 19.5 ± 0.7 |
| 8 | 10 | 36.70 ± 0.15 | 26.6 ± 2.2 | 18.8 ± 0.4 |
| 9 | 10 | 36.47 ± 0.21 | 28.2 ± 0.8 | 19.8 ± 0.8 |

TABLE 5-continued

Strength and Stiffness for Three Point Bend Testing of Plates

| DOE Run # | Number of Samples Tested | Specimen Length (mm) | Strength (Peak Load) (N) | Stiffness (Slope) (N/mm) |
|---|---|---|---|---|
| 10 | 10 | 37.55 ± 0.22 | 38.2 ± 1.7 | 19.3 ± 0.6 |
| 11 | 10 | 36.61 ± 0.18 | 26.4 ± 1.1 | 18.6 ± 0.6 |
| 12 | 10 | 36.54 ± 0.50 | 28.9 ± 1.1 | 20.0 ± 1.5 |
| 13 | 10 | 36.81 ± 0.51 | 27.3 ± 1.0 | 19.5 ± 0.7 |
| 14 | 9 | 36.82 ± 0.62 | 28.2 ± 1.6 | 15.4 ± 0.5 |
| 14 run a 2nd time | 10 | 36.02 ± 0.15 | 28.5 ± 1.0 | 20.8 ± 1.7 |
| 15 | 10 | 36.87 ± 0.60 | 27.5 ± 1.4 | 20.3 ± 1.4 |
| 16 | 10 | 36.47 ± 0.56 | 28.0 ± 2.1 | 20.8 ± 1.3 |

It is concluded that the mechanical strength is affected slightly by the interaction of ethylene oxide concentration and steam time, however, this effect is considered very small.

Figure 2:
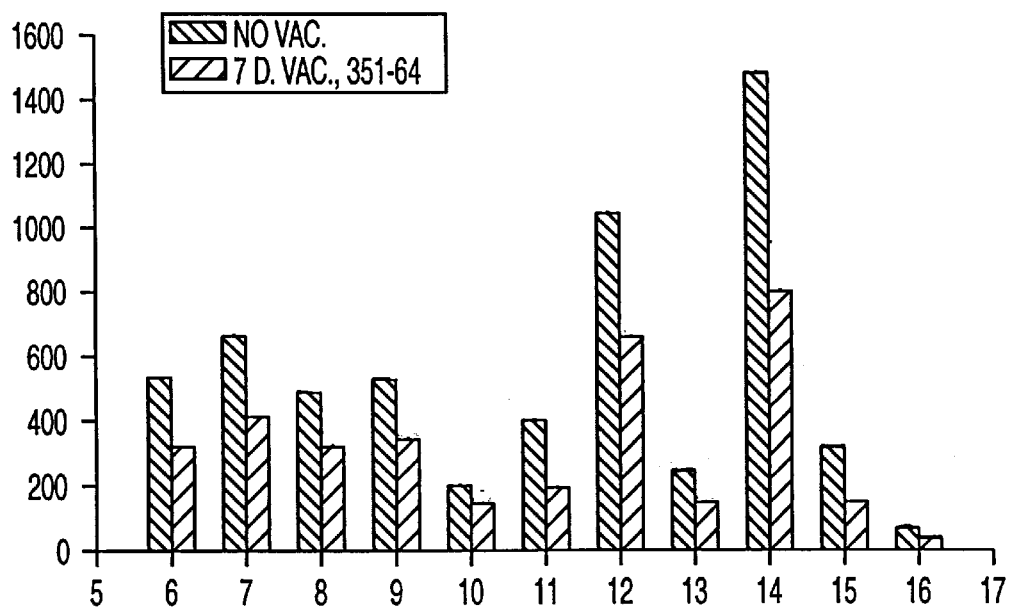
FIG. 2 illustrates the effect of deep vacuum degassing of plates at $10^{-7}$ Torr, 37° C. on ethylene oxide residue after 1 week.
Figure 3:
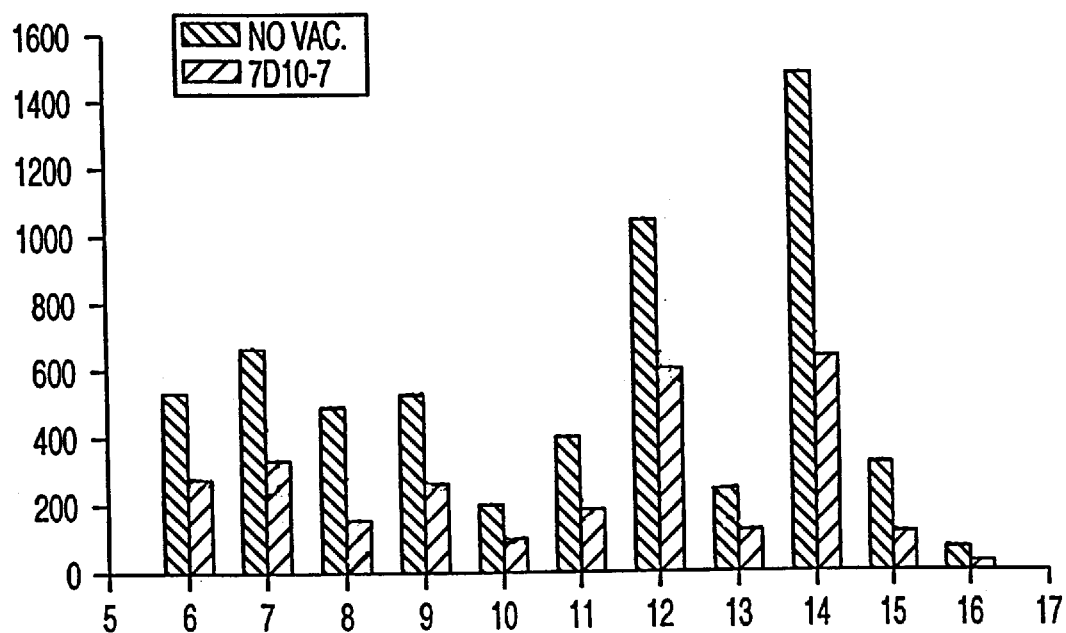
FIG. 3 illustrates the effect of deep vacuum degassing of plates at $10^{-7}$ Torr, 37° C. on ethylene oxide residue after 2 weeks.

Ethylene oxide residue in the device after the reaction with steam was measured before degassing in the original package, after one week of degassing, and after two weeks of degassing at $10^{-7}$ Torr at 37° C. as shown in FIGS. 1, 2 and 3 respectively.

The data also indicates that the removal of the ethylene oxide by post reaction vacuum degassing slowed down considerably during the second week of degassing, but still continued during this period.

It is not intended that the example given here should be construed to limit the invention, but rather it is submitted to illustrate some of the specific embodiments of the invention. Various modifications and variations of the present can be made without departing from the scope of the appended claims.

What is claimed is:

1. A method for reducing residual ethylene oxide levels comprising reacting a portion of the residual ethylene oxide remaining in or on a sterilizable material after a sterilization procedure is completed with steam at a pressure of between 1.3 and about 1.6 psia for at least three hours at a temperature between about 110° F. and about 125° F. to form ethylene glycol.

2. The method of claim 1 further comprising keeping the ethylene glycol level at or below about 5000 parts per million.

3. The method of claim 1 wherein the stern is introduced into a sterilization chamber containing the sterilized material.

4. The method of claim 1 wherein the stern is reacted with the residual ethylene oxide for a period of time in the range of about 3 hours to about 15 hours.

5. The method of claim 1 wherein the stern is reacted with the residual ethylene oxide for a period of time in the range of about 3 hours to about 13 hours.

6. The method of claim 1 wherein the stern is reacted with the residual ethylene oxide for a period of time of about 10 hours.

7. The method of claim 1 wherein the sterilizable material is a polymeric material.

8. The method of claim 7, wherein the polymeric material is a bioabsorbable polymer.

9. The method of claim 7 wherein the polymeric material is an amorphorus or semicrystalline polymer.

10. The method of claim 8 wherein the bioabsorbable polymer is in the form of a bioabsorbable medical device.

11. The method of claim 1 wherein a deep vacuum in a range of about $10^{-6}$ Torr to about $10^{-8}$ Torr is applied to the sterilizable material after the reaction of residual ethylene oxide with stern.

12. The method of claim 1 wherein a deep vacuum in a range of about $10^{-7}$ Torr is applied to the sterilizable material after the reaction of residual ethylene oxide with stern.

13. The method of claim 11 wherein a temperature in a range of about 20° C. to about 55° C. is maintained during the application of deep vacuum.

14. The method of claim wherein a temperature of about 37° C. is maintained during the application of deep vacuum.

15. The method of claim 11 wherein the deep vacuum is applied for a range of about 1 day to about 3 weeks.

16. The method of claim 11 wherein the deep vacuum is applied for about 2 weeks to about 3 weeks.

17. A method for reducing residual ethylene oxide levels after a sterilization procedure comprising the steps of:

placing a sterilizable material in a sterilization chamber at an ethylene oxide concentration of about 300 mg/l to about 800 mg/l, for about 3 seconds to about 10 hours dwell time to effect the sterilization of the sterilizable material; and then subjecting the sterilizable material to a post sterilization treatment comprising subjecting the sterilizable material a time of about three hours to about 15 hours of pulsed or continuous steam at about 1.3 to about 1.6 psia pressure and about 110° F. to about 125° F. to reduce residual ethylene oxide levels.

18. The method of claim 17 wherein the pulsed or continuous steam is at about 1.3 to about 1.4 psia pressure and about 1 18° F. to about 120° F.

19. The method of claim 17 further comprising subjecting the sterilizable material to about 2 weeks to about 3 weeks of deep vacuum degassing following the post sterilization treatment with pulsed or continuous steam.

20. The method of claim 17 wherein the ethylene oxide concentration is about 600 mg/l.

21. The method of claim 20 wherein the dwell time is about 2½ hours.

22. The method of claim 20 further comprising selecting a time of about 2½ hours as the dwell time.

23. The method of claim 22 wherein the post sterilization treatment time is about 3 hours to about 13 hours.

24. The method of claim 22 wherein the post sterilization treatment time is about 10 hours.

25. A method for reducing residual ethylene oxide levels after a sterilization procedure comprising the steps of:

placing a sterilizable material in a sterilization chamber at an ethylene oxide concentration of about 600 mg/l, for 3 seconds to about 10 hours dwell times to effect the sterilization of the sterilizable material; and then subjecting the sterilizable material to a post sterilization treatment comprising subjecting the sterilizable material for about 3 hours to about 15 hours of pulsed or continuous steam at about 1.0 to about 1.6 psia pressure and about 110° F. to about 125° F. followed by deep vacuum degassing of about $10^{-6}$ to about $10^{-8}$ Torr and about 20° C. to about 55° C. for at least one day to reduce residual ethylene oxide levels.

* * * * *

UNITED STATES PATENT AND TRADEMARK OFFICE
CERTIFICATE OF CORRECTION

PATENT NO. : 6,231,810 B1  Page 1 of 1
DATED : May 15, 2001
INVENTOR(S) : Tunc

It is certified that error appears in the above-identified patent and that said Letters Patent is hereby corrected as shown below:

Column 9,
Line 47, "stern" should read -- steam --.
Line 48, "sterilized" should read -- sterilizable --.
Line 50, "stern" should read -- steam --.
Line 53, "stern" should read -- steam --.
Line 56, "stern" should read -- steam --.

Column 10,
Line 4, "stern" should read -- steam --.
Line 8, "stern" should read -- steam --.
Line 12, after "claim" insert -- 11 --.
Line 29, after "material" insert -- for --.
Line 35, "1 18°" should read -- 118° --.
Line 45, cancel "further comprising selecting"; and after "20" insert -- wherein --.
Line 46, cancel "a time of about 21/2 hours as"; and after "time" insert -- is about 0.5 hours to about 5 hours --.

Signed and Sealed this

Nineteenth Day of February, 2002

Attest:

*Attesting Officer*

JAMES E. ROGAN
*Director of the United States Patent and Trademark Office*